United States Patent
MacPhee et al.

(10) Patent No.: US 6,682,648 B1
(45) Date of Patent: Jan. 27, 2004

(54) ELECTROCHEMICAL REPORTER SYSTEM FOR DETECTING ANALYTICAL IMMUNOASSAY AND MOLECULAR BIOLOGY PROCEDURES

(75) Inventors: Robert D. MacPhee, Los Angeles, CA (US); Clive R. Taylor, Los Angeles, CA (US); Rainer Hintsche, Itzehoe (DE); Rene Seitz, Itzehoe (DE)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/105,538

(22) Filed: Jun. 26, 1998

Related U.S. Application Data

(60) Provisional application No. 60/055,759, filed on Aug. 14, 1997, and provisional application No. 60/055,466, filed on Aug. 12, 1997.

(51) Int. Cl.[7] ............................................... G02N 27/26
(52) U.S. Cl. ................................... 205/777.5; 204/403
(58) Field of Search ....................... 204/403; 205/777.5; 435/817

(56) References Cited

U.S. PATENT DOCUMENTS

| | | | |
|---|---|---|---|
| 4,444,878 A | 4/1984 | Paulus | 435/7.1 |
| 4,840,893 A | 6/1989 | Hill et al. | |
| 4,963,245 A | 10/1990 | Weetall | |
| 4,978,610 A | * 12/1990 | Forrest et al. | 205/777.5 |
| 5,149,629 A | * 9/1992 | Rishpon et al. | 435/7.9 |
| 5,312,527 A | 5/1994 | Mikkelsen et al. | 205/777.5 |
| 5,391,272 A | 2/1995 | O'Daly et al. | |
| 5,622,872 A | 4/1997 | Ribi | 436/518 |
| 5,670,031 A | 9/1997 | Hintsche et al. | |

FOREIGN PATENT DOCUMENTS

| | | |
|---|---|---|
| DE | 43 18519 A1 | 6/1993 |
| EP | 0 859 229 A | 8/1998 |
| JP | 2119799 | 5/1990 |
| WO | WO 86 05815 A | 10/1986 |
| WO | WO 94/29708 | 12/1994 |
| WO | WO 97/16712 | 5/1997 |
| WO | WO 99/07879 | 8/1998 |

OTHER PUBLICATIONS

Docherty, et al., The magnetic immuno–polymerase chain reaction assay for the detection of Campylobacter in milk and poultry, Lett. Appl. Microbiol. 22(4):288–92 (1996). month unknown.

Gil, et al., Covalent binding of urease on ammonium–selective potentiometric membranes, Biosens. Bioelectron. 7(9):645–52 (1992). month unknown.

Hintsche, et al., Direct electrical detection of affinity binding without labeling, Proceedings of Eurosensors X, The 10th European Conference on Solid–State Transducers, vol. 5 of 5, Leuven Sep. 8–11 (1996).

Hintsche, et al., Microbiosensors using electrodes made in Si–technology, EXS. 80:267–83 (1997). month unknown.

Letellier, et al., Performance evaluation of automated immunoassays on the Technicon Immuno 1 system, Clin. Chem. 42(10):1695–701 (1996). month unknown.

Niwa, et al., Small–volume voltammetric detection of 4–aminophenol with interdigitated array electrodes and its application to electrochemical enzyme immunoassay, Anal. Chem. 65(11):1559–63 (1993). month unknown.

Paeschke, et al., Properties of interdigital electrode arrays with different geometries, Analytica Chimica Acta 305:126–136 (1995). month unknown.

(List continued on next page.)

*Primary Examiner*—T. Jill Warden
*Assistant Examiner*—Alex Noguerda

(57) ABSTRACT

An immunochemical and molecular biologic endpoint reporter system in which reaction products, coupled to electrochemically active molecules susceptible to redox recycling or coupled to enzymes capable of proportional generation of said electrochemically active molecules, are detected and/or quantitated using amperiometry in conjunction with a silicon microchip possessing a closely spaced interdigitated array of nobel metal electrodes.

25 Claims, 9 Drawing Sheets-

OTHER PUBLICATIONS

Paeschke, Doctoral Dissertation, Dunnfilm Metallelektroden als elektrochemische Verstarker und dielektrische Transducer. Feb. 1997 1st & 2nd page of Section 3.4.4.

Rossomando, et al., Immunomagnetic separation of tumor necrosis factor alpha. I. Batch procedure for human temporomandibular fluid, J. Chromatogr. 583(1):11–8 (1992). month unknown.

Rossomando, et al., Immunomagnetic separation of tumor necrosis factor alpha. II. In situ procedure for the human gingival space, J. Chromatogr. 583(1):19–26 (1992). month unknown.

Santandreu, et al., Amperometric immunosensors based on rigid conducting immunocomposites, Anal. Chem. 69(11):2080–5 (1997). month unknown.

Santandreu, et al., Development of electrochemical immunosensing systems with renewable surfaces, Biosens. Bioelectron. 13(1):7–17 (1998).

Seitz, et al., Novel enzyme labels for electrochemical micro–ELISA, Fourth World Congress on Biosensors (Abstracts) (1996). month unknown.

Seitz, et al., Immunosensing of anti–viral antibodies using microelectrode arrays, Proceedings of Eurosensors X, The 10th European Conference on Solid–State Transducers, vol. 3 of 5, Leuven Sep. 8–11 (1996).

Sole, et al., Flow injection immunoanalysis based on a magnetoimmunosensor system, Anal. Chem. 70(8):1462–7 (1998). month unknown.

Weetall, et al., A simple, inexpensive, disposable electrochemical sensor for clinical and immuno–assay, Biosensors 3(1):57–63 (1987–88). month unknown.

Wollenberger, et al., Interdigitated array microelectrodes for the determination of enzyme activities, Analyst 119:1245–1249 (1994).

Translated abstract for JP 2119799 (Reference BA).

Morf, The Principles of Ion–Selective Electrodes and of Membrane Transport, Studies in Analytical Chemistry 2 (1981) pp. v–xi and 1–347.

Rechnitz, Bioselective Membrane Electrode Probes, Science 214:287–291 (Oct. 1981).

Tang, H.T., et. al., p–Aminophenyl Phosphate: An Improved Substrate for Electrochemical Enzyme Immunoassay, Analytica Chimica Acta, 214: 187–195 (1988). month unknown.

Duan, C. and Meyerhoff, M.E., Separation–Free Sandwich Enzyme Immunoassays Using Microporous Gold Electrodes and Self–Assembled Monolayer/Immobilized Capture Antiboeis, Anal. Chem. 66: 1369–1377 (May 1994).

Meyerhoff, M.E., et. al., Novel Nonseparation Sandwich–Type Electrochemical Enzyme Immunoassay System for Detecting Marker Proteins in Undiluted Blood, Clincal Chemistry 41(9): 1378–1384 (1995). month unknown.

Dewar, R. L., et. al., Application of Branched DNA Signal Amplification to Monitor Human Immunodeficiency Virus Type 1 Burden in Human Plasma, Journal of Infectious Diseases 170:1172–1179 (1994). month unknown.

Gehring A.G., et. al., Enzyme–linked immunomagnetic electrochemical detection of Salmonella typhiimurium, Journal of Immunological Methods, 195(1):15–25 (1996). month unknown.

\* cited by examiner

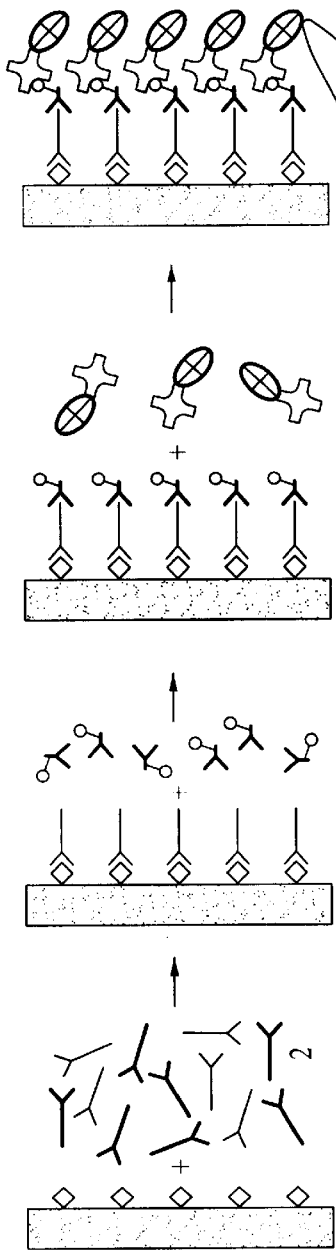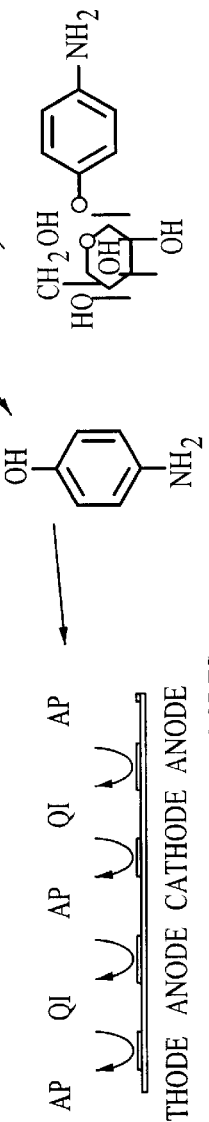
Fig. 2

| SPECIMEN NO. | COMMERCIAL ABBOTT | MIX AND MATCH HPO | MIX AND MATCH B-GAL |
| --- | --- | --- | --- |
| 1 | 14000 | 125000 | 11000 |
| 2 | 4400 | 6000 | 8000 |
| 3 | 300 | 500 | 450 |
| 4 | 1500 | 1000 | 2500 |
| 5 | 2000 | 1200 | 1700 |
| 6 | 1700 | 1100 | 2000 |
| 7 | NEG | NEG | NEG |
| 8 | NEG | NEG | NEG |
| 9 | NEG | NEG | NEG |
| 10 | NEG | NEG | NEG |

| REGRESSION OUTPUT: | |
|---|---|
| CONSTANT | -390.639 |
| STD ERR OF Y EST | 1003.611 |
| R SQUARED | 0.944968 |
| NO. OF OBSERVATIONS | 10 |
| DEGREES OF FREEDOM | 8 |
| X COEFFICIENT(S) | 1.021692 |
| STD ERR OF COEF. | 0.087172 |

REGRESSION OUTPUT:

| | |
|---|---|
| CONSTANT | -532.449 |
| STD ERR OF Y EST | 1315.275 |
| R SQUARED | 0.956282 |
| NO. OF OBSERVATIONS | 9 |
| DEGREES OF FREEDOM | 7 |
| X COEFFICIENT(S) | 1.063981 |
| STD ERR OF COEF. | 0.085985 |

REGRESSION OUTPUT:

| | |
|---|---|
| CONSTANT | 28683.7 |
| STD ERR OF Y EST | 24357.31 |
| R SQUARED | 0.994604 |
| NO. OF OBSERVATIONS | 5 |
| DEGREES OF FREEDOM | 3 |
| X COEFFICIENT(S) | 0.88036 |
| STD ERR OF COEF. | 0.037439 |

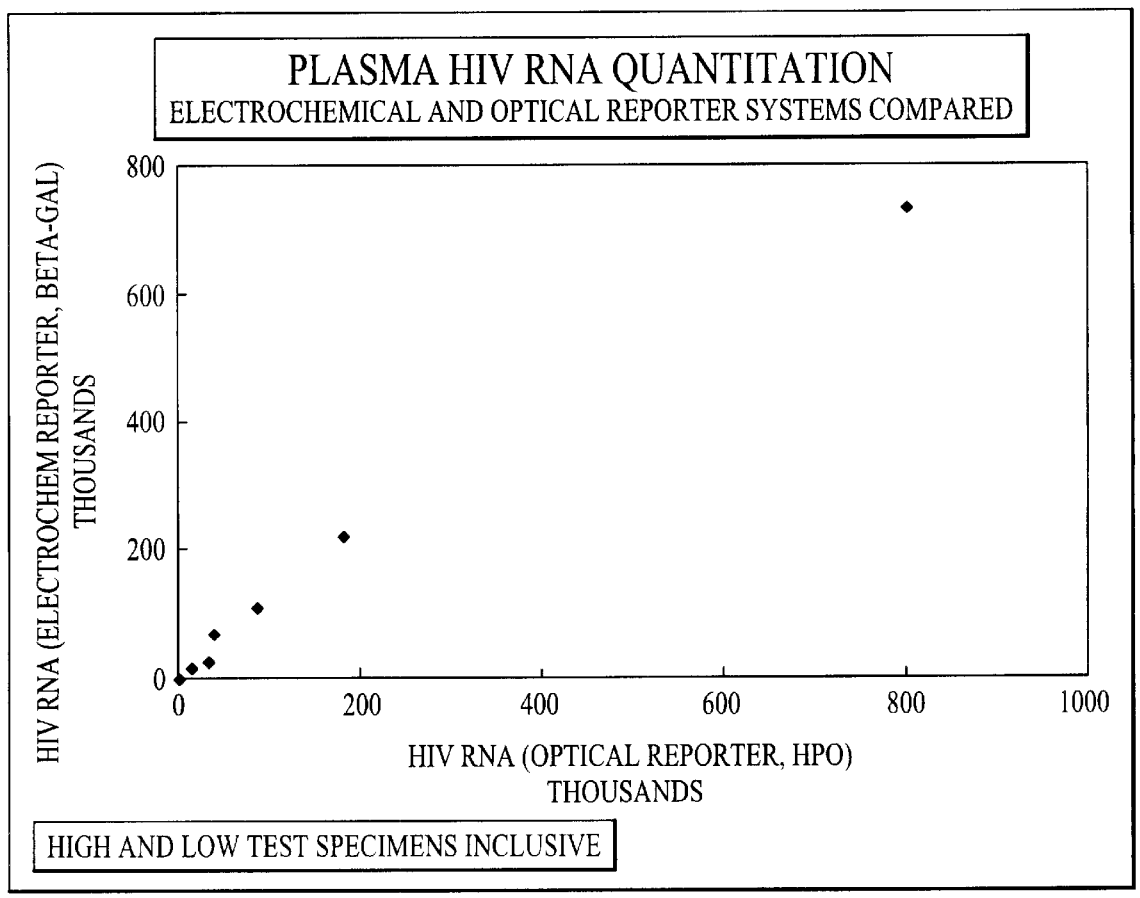

ELECTROCHEMICAL REPORTER SYSTEM FOR DETECTING ANALYTICAL IMMUNOASSAY AND MOLECULAR BIOLOGY PROCEDURES

This application claims benefit under 35 U.S.C. §119(e) of U.S. Provisional Application No. 60/055,759, filed Aug. 14, 1997, and U.S. Provisional Application No. 60/055,466, filed Aug. 12, 1997 (which are incorporated herein by reference in their entirety).

FIELD OF INVENTION

The present invention relates to an electrochemical method and an associated microchip-based apparatus that can be used to afford voltammetric or amperiometric detection for monitoring immunochemical and/or molecular biology procedures.

BACKGROUND OF INVENTION

To assess the-utility of any chemical reaction, whether it be inorganic, organic or biochemical, the composition and relative quantities of reactants and products must be determined while the reaction is in progress or at its equilibrium endpoint. One specific means of affecting such monitoring utilizes biologic or non-biologic molecules capable of binding to either reactant or product molecules in a structure restricted manner. These analytic techniques are, in general, referred to as immunochemical, in reference to the selective recognition and binding capacity of immunoglobulins, even though substances other than antibodies may serve as recognition molecules. The terms receptor and ligand have been used to more generally describe this area of analytic art. Although diversely applied in basic organic and biochemistry, these techniques have seen their most prolific development in the field of clinical medicine, and relevant generalized principles for measuring the progress of reactions immunochemically, although applicable to many other scientific pursuits, can be illustrated using examples from this field. Here, a multitude of immunochemically formatted tests have been developed for measuring virtually any biologic molecule of clinical importance. Such analytic procedures represent the cornerstones for laboratory studies in toxicology, endocrinology, immunology, serology, microbiology, and enzymology, to name but a few.

The most frequently utilized methods at present, are the enzyme-linked immunosorbant assays (ELISAs). These procedures are applicable to a wide variety of fields such as biotechnology, environmental protection and public health. The performance of these conventional state of the art calorimetric methods of detection suffer from the infirmities of having requirements for optical clarity, photomultiplication, signal digitalization or analog quantitation and transmission, viscosity or background chromogenic neutrality.

In the immunochemistry field, for example, enzyme immunoassays (EIA) and, more particularly enzyme-linked immunosorbent assays (ELISA) are well known in the art and have become important and relatively cost-efficient tools of clinical laboratories for detecting traces of foreign substances, such as antigens or antibodies in body fluids and tissues. (See, e.g. Immunoassay, Diamandis, E. and Christopoulos, T. eds., (1996); Clausen, J., Immunochemical Techniques for the Identification and Estimation of Macromolecules (Laboratory Techniques in Biochemestry and Molecular Biology) Vol. 1 (1989); Tijssen, P., Practice and Theory of Enzyme Immunoassays (Laboratory Techniques in Biochemistry and Molecular Biology), (1985); Principles and Practice of Immunoassay, 2d ed., Price, C. and Newman, D., eds. (1997)—which are hereby incorporated by reference in their entirety.)

Such immunoassays, while generally reliable, depend on sophisticated and extremely expensive optical processes to report their results. Such optical processes are cumbersome because they are expensive, require a clean and unsoiled measurement chamber and their visually rendered signals prevent precise quantitation of results in a simple manner. State of the art optical systems have several drawbacks, in that they generally require optical clarity, photo multiplication, signal digitalization or analog quantitation and transmission, as well as compatible viscosity and/or a neutral optical background. Transparent support media, aqueous or otherwise, may become fouled or turbid and prevent or render difficult any accurate analyses utilizing optical reporters.

Attempts have been made to provide systems other than optical ones to detect antigens in body fluids. Duan, C. et al., "Separation-Free Sandwich Enzyme Immunoassays Using Microporous Gold Electrodes and Self-Assembled Monolayer/Immobilized Capture Antibodies," Analytical Chemistry, 66/9:1369–77 (1994) discloses a separation-free system aimed at simplifying conventional immunoassay protocols utilizing a gold-plated microporous-membrane which serves as the solid phase for a noncompetitive sandwich-type immunoassay as well as a working electrode of an amperiometric detection system. A capture monoclonal antibody is covalently immobilized by a conventional chemical bonding agent at the gold plated side of the membrane. A model analyte protein as well as an alkaline phosphatase labeled antibody are incubated simultaneously with the immobilized capture antibody. Surface bound antibody is then separately detected from any excess conjugate in the sample by the introduction of an enzyme substrate, such as 4-aminophenol phosphate, from the backside of the membrane which is not gold-plated. The substrate seeps through the membrane and encounters the bound enzyme antibody conjugate at the gold-plated surface. Aminophenol is thus enzymatically generated and detected by oxidation at the gold electrode, the magnitude of the current being a measure of the concentration of analyte in the sample. However, the sensitivity of the system disclosed in Duan is very low, requiring a 20 nA signal compared to 0.1 nA in the present invention. This translates to a 50 times sensitivity advantage when considering actual protein detection limits. The system described by Duan was only capable of detecting protein (human chorionoic gonadotropin) down to a level of 500 ng/l, whereas the novel methodology herein described has shown a 10 ng/l protein detection limit.

In another experiment reported in Meyerhoff, M. et al., "Novel Nonseparation Sandwich-Type Electrochemical Enzyme Immunoassay System for Detecting Marker Proteins in Undiluted Blood," Clinical Chemistry, 41/9:1378–1384 (1995), a similar microporous membrane was utilized in a non-separation sandwich-type electrochemical enzyme immunoassay system for detecting marker proteins in undiluted blood. However, this method is limited to prostate specific antigen (PSA) measurement in blood. The method described in this reference demonstrates no additional sensitivity when compared to the aforementioned article by Duan. Rather it simply describes the application of the technique to the measurement of an additional protein moiety (prostate specific antigen, PSA). Niwa, O. et al., "Small-Volume Voltammetric Detection of 4-Aminophenol with Interdigitated Array Electrodes and Its Application to Electrochemical Enzyme Immunoassay," Analytical Chemistry, 65:1559–1563 (1993) have reported on the use of an interdigitated array (IDA) micro-electrode cell in small-volume voltammetric detection of 4-aminophenol. However, Niwa used only alkaline phosphatase and used a sensor with a relatively small sensing area measuring 2×2 mm and relatively large electrodes of width of 3 to 5 μm, spaced 2 or 5 μm from each other. Furthermore, their detection range was from 10 to 1,000 ng/ml for mouse IgG molecules above 1,000 nmol/l for p-aminophenol, which is about 100 times less sensitive than the present invention and does not make his technique viable for clinical applications with respect to disease-specific antibody detection and quantification.

H. T. Hang et al., in Anal. Him. Acta, 214:187–95 (1988) describes a system for the electrochemical detection of low molecular weight digoxin in the context of an immunoassay, but registers only currents generated by the oxidation of p-aminophenol.

Likewise in the molecular biology field, it is equally important to determine the composition and relative quantities of reactants and products while the reaction is in progress or at its equilibrium endpoint. One specific means of affecting such monitoring utilizes biologic or non-biologic labeling or reporter molecules capable of binding either reactant or product molecules in a structure-restricted manner. Many procedures commonly performed in the field of molecular biology fall into this category. Nucleic acid reactants or products have for many years been directly labeled by a variety of means such as the incorporation of radioactive 32-P or 3-H, or the use of electrophoretic gels incorporating intercalcating fluophores such as ethidium bromide. More recently, techniques have been borrowed from the immunochemical or receptor-ligand field and adapted to provide reporter systems that are safer, environmentally friendly, more cost effective, far faster, appropriate for use in a wide range of methods and compatible with efficiently conducting large numbers of procedures. Reporters have recently been introduced into the field of molecular biology that include detection by fluorescence, chemiluminescence, and colorimetry. These labels have been linked or conjugated directly to nucleic acid reactants or products, as well as generated indirectly via nucleic acid-enzyme conjugates in a manner comparable to ELISA techniques. (See, e.g., Tijssen, P., Hybridization With Nucleic Acid Probes: Theory and Nucleic Acid Probes, Vol. 1 (1993); Tijssen, P., Hybridization With Nucleic Acid Probes: Probe Labeling and Hybridization Techniques, Vol. 2 (1993); Meier, T. and Fahrenholz, F. eds., A Laboratory Guide To Biotin-Labeling in Biomolecule Analysis, BioMethods Vol. 7 (1996); Garman, A., Non-Radioactive Labelling: A Practical Introduction (Biological Techniques Series)(1997); Agrawal, S. ed., Protocols for Oligonucleotide Conjugates: Synthesis and Analytical Techniques (Methods in Molecular Biology, Vol. 26) (1993); Burden and Whitney, Biotechnology: Proteins to PCR: A Course in Strategies and Lab Techniques (1995)—which are hereby incorporated by reference in their entirety.) Detection of specific nucleic acid moieties using such reporters can be effectively performed while the reaction is in progress (rate measurement or kinetic measurement), or when the reaction has reached equilibrium (endpoint reporting). Molecular biology procedures using such reporter systems are commonly applied in many fields such as biotechnology, environmental protection and public health.

More specifically, recent advances in signal amplification methods (Dewar R. L., et al., "Application of Branched Chain DNA Signal Amplification to Monitor Human Immunodeficiency Virus Type 1 Burden in Human Plasma," Jrnl of Inf. Dis., Vol 170:1172–1179 (1994) as well as template amplification methods have resulted in a surge of nucleic acid detection and measurement techniques utilizing enzymatic conjugates in conjunction with calorimetric or chemiluminescent reporter products in place of the more hazardous, eco-unfriendly and temporally inefficient conventional radiographic reporters. All of these new reporters have, to present, relied on optical detection methods which, unfortunately, suffer from the infirmities of having requirements for solution clarity, photomultiplication, complex signal digitalization or analog quantitation and transmission, viscosity restrictions and requisite background chromogenic neutrality.

Therefore, despite all of these attempts at improvement, it is still the case that none of these systems describe an electrochemically detected enzyme-conjugate/reporter substrate capable of providing a cost effective method for direct testing of unprocessed immunochemical and biological samples with a satisfactory level of detection sensitivity.

SUMMARY OF THE INVENTION

It is the object of the present invention to provide an immunochemical and molecular biological reporter system to detect and quantify reactants or products. The present invention is intended to include both endpoint and kinetic reporting applications. This system consists of a silicon microchip-formatted interdigitated array (IDA) of closely spaced nobel metal electrodes used to detect immunochemical or nucleic acid conjugates containing electrochemically active molecules susceptible to redox recycling and therefore detectable by means of amperiometry or voltammetry.

It is a further object of the present invention to provide a system which can substitute for conventional calorimetric enzyme reporter systems to achieve enhancement relative to performance and economy.

It is a further object of the present invention to reduce the time necessary for completion of broad capacity for analytic procedures.

It is a further object of the present invention to increase the detection sensitivity relative to the absolute number of reporter molecules and the volume of solution required for their detection.

It is a further object of the present invention to expand the linear range of concentrations over which reporter molecules may be detected and quantitated.

It is a further object of the present invention to broaden the capacity for miniaturization and simplification of equipment relating to both methodologic and detection components supporting both hand-held as well as large-scale high throughput applications.

It is a further object of the present invention to eliminate the sample solution optical clarity or ambient optical density requirements.

It is a further object of the present invention to be able to use microliter or lower specimen requirements which correlates with reduced reagent costs.

It is a further object of the present invention to have manufacturing costs of IDA substantially in comparison to principle components photomultiplier requirements in comparable optical reporter systems.

In one preferred embodiment, this electrochemical reporter system may be applied to an immunochemical method for directing antibodies arising as a result of a viral infection by utilizing an immunoassay including a multivalent enzyme conjugate (Biotin/Avidin) for liberating redox-active molecules, and an IDA for measuring the redox-active molecules. In addition to the first embodiment, this novel reporter system is equally applicable to all enzyme-labeled immunochemistry formats. Methods to which this system applies are commonly, but not exclusively used to examine 1) Infectious diseases (microbial antigen or antibody proteins); 2) Autoimmune diseases (autoantigen or autoantibody proteins); 3) oncologic markers (so-called tumor specific proteins or steroids); 4) Endocrine hormones (polypeptides, thyronines and steroids); and 5) Therapeutic drugs or toxicologic materials.

In another preferred embodiment, this novel electrochemical reporter system may be applied to detecting or quantifying specific nucleic acids or their amplicons in analytic molecular biologic procedures. Analyses of specific nucleic acids or nucleic acid sequences are gaining wide acceptance and use in the clinical setting to examine body fluids or tissues for the presence of infectious microorganisms, malignancy, inherited disease (genetic defects), forensic medical evidence, and paternity/maternity identification.

BRIEF DESCRIPTION OF THE DRAWINGS

The novel features which are considered to be characteristic of the invention are set forth with particularity in the appended claims. The invention itself, however, in respect of its structure, construction, and lay-out, as well as manufacturing techniques, together with other objects and advantages thereof, will be best understood from the ensuing description of preferred embodiments, when read in connection with the appended drawings, in which:

FIGS. 2 and 3 are schematic presentations, including legends, describing the application of the electrochemical reporter system, in accordance with the invention, to differing immunochemical procedural formats. FIG. 2 exemplifies a non-competitive immunoassay employing a multi-valent labeling conjugate consisting of a biotinylated labeling antibody paired with an avidin-conjugated electrochemical reporter. FIG. 3 exemplifies a competitive immunoassay format in which the labeling antibody (monovalent, and conjugated to the electrochemical reporter) is displaced by an antibody, the analyte, with similar binding specificity.

FIGS. 7, 8, and 9 are charts which graphically and statistically compare HIV RNA quantitation results derived following RT PCR and using two matched amplicon detection procedures which differ in the reporter conjugate employed. An electrochemical reporter in accordance with the invention is used in one detection procedure, and an optical reporter is used in the comparative detection procedure.

DETAILED DESCRIPTION OF INVENTION

Figure 1:
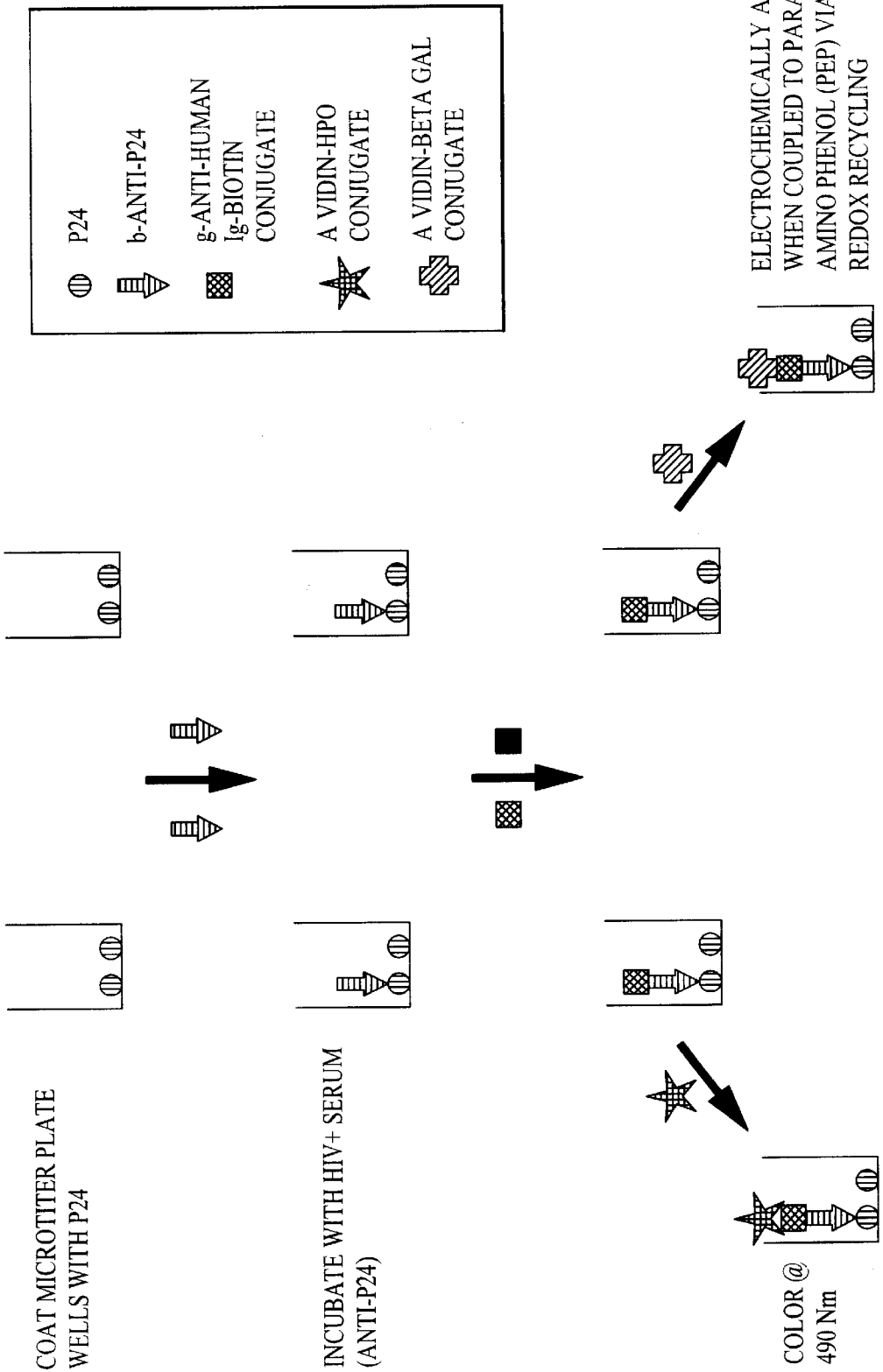
FIG. 1 is a schematic presentation describing a pair of ELISA methods which exemplify the use of optical and electrochemical reporter systems in the immunochemical art.

In its broadest aspect, this electrochemical reporter technology is capable of endpoint detection or kinetic monitoring of clinical and analytical immunochemical and molecular biology procedures including analytical and clinical applications. The present invention employs a closely spaced (nanometer scale) interdigitated array of thin film nobel metal microelectrodes to detect voltammetric signals produced in proportion to the concentration of organic (or inorganic) reporter molecules capable of exhibiting redox recycling at the electrode's surface. The anodes and cathodes in the interdigitated array may have a width between about 100 and about 800 nm. Preferred are interdigitated arrays where the widths of the anodes and cathodes is between about 150 and about 650 nm. Most preferred are arrays with anodes and cathodes having a width of about 300 nm. The electrodes may be spaced apart from each other with a distance between about 100 and about 800 nm. Preferred are distances of about 100 to about 650 nm. Most preferred are distances of about 300 nm. The application of the present invention may use ganged IDAs in which a single multipotentiostat is used to detect signals from several IDAs on a single chip, so that when in use, the readout(s) show the reaction status of each IDA, as well as combined amperiometric reading(s).

The electrochemical labels may be directly conjugated to the reporter substance, or generated as conjugated or unconjugated products of enzyme/substrate reactions in conjunction with ligand/receptor procedures. Enzyme/substrates which may be used with the present invention include, but are not limited to, α-galactosidase/p-aminophenyl-α-D-galactopyranoside, β-galactosidase/p-aminophenyl-β-D-galactopyranoside, α-glucosidase/p-aminophenyl-α-D-glucopyranoside, β-glucosidase/p-aminophenyl-β-D-glucopyranoside, α-mannosidase/p-aminophenyl-α-D-mannopyranoside, β-mannosidase/p-aminophenyl-β-D-mannopyranoside, acid phosphatase/p-aminophenylphosphate, alkaline phosphatase/p-aminophenylphosphate, and phosphodiesterase II/p-aminophenylphosphorylcholine.

Immunochemistry

Immunoassays for detecting an indicative species have been adapted to numerous procedural formats. For example, relevant. reactions may all take place in solution, or specific components may be anchored to solid supports for ready separation of bound ligands. Further examples of format variety include the use of labeled recognition molecules to directly indicate the presence of a substance of interest (non-competition assay), or specific recognition molecules, in selectively limited quantities, may be reacted with a sample containing the endogenous substance of interest as well as a known quantity of an exogenous label, with similar binding characteristics as the substance of interest, but conjugated with a detectable label. In such a format (competition assay), the quantity of labeled material complexed to the recognition molecules will be dependent on the relative ratios of the endogenous (sample) and exogenous (label) molecules. The conjugate is not necessarily restricted to the molecular species eventually subjected to detection. In the preferred immunoassay example, the EIA or ELISA, protein analytes contained in a given sample as antibodies are, for instance, bound to an antigen or capture antibody. Subsequently, the sample matrix is washed off, and the analyte is bound in a quantitative relationship to an enzyme label after another washing step to remove the excess enzyme-labeled antibodies. If calorimetric detection is to be utilized, the quantity of enzyme attached to the solid phase may be determined by adding a specific substrate and measuring the amount or rate of enzymatically generated colored product. This endpoint quantity or rate is a proportional measure of the amount of antigen present in the specimen.

The electrochemical reporter system can be generally substituted in place of conventional calorimetric or chemiluminescent enzyme-linked immunoassay reporters and applied throughout the existing range of analytical test formats. These methodologies are commonly, but not exclusively, used to examine blood or other body fluids for the presence of substances associated with: 1) Infectious diseases (microbial antigen or antibody proteins); 2) Autoimmune diseases (autoantigen or autoantibody proteins); 3) Oncologic markers (so-called tumor specific proteins or steroids); 4) Endocrine hormones (polypeptides, thyronines and steroids); and 5) Therapeutic drugs or toxicologic materials.

In the first embodiment, the invention is used to detect antigens or antibodies. The term "antibody" refers to immunoglobulins of any isotype or subclass as well as any fab or fe fragment of the aforementioned. Antibodies of any source are applicable including polyclonal materials obtained from any animal species; monoclonal antibodies from any hybridoma source; and all immunoglobulins (or fragments) generated using viral, prokaryotic or eukaryotic expression systems. Biologic recognition molecules other than antibodies, are equally applicable for use with the current invention. These include, but are not limited to: cell adhesion molecules, cell surface receptor molecules, and solubilized binding proteins. Non-biologic binding molecules, such as "molecular imprints" (synthetic polymers with predetermined specifically for binding/complex formation), are also applicable to the invention. The terms "antigens," "immunogens" or "haptens" refer to substances which can be recognized by in vivo or in vitro immune elements, and are capable of eliciting a cellular or humoral immunologic response. Although the electrochemically active reporter utilized in the embodiment is specified as para-aminophenol (generated by the action of a beta-galactosidase conjugate in conjunction with a specific substrate), it should be noted that the invention is generally applicable to molecules capable of redox recycling, and enzyme systems capable of generating such reporters.

In particular, the embodiment will be described in the context of electrochemical detecting antibody to the human immunodeficiency virus (HIV). More specifically, the detection of antibodies developed in vivo as a result of infection with the human immunodeficiency virus.

An electrochemical sensor comprised of an array of interdigitated micro electrodes of the kind useful in the practice of the present invention is published in International Patent Application having PCT Publication No. WO 94/29708 (published Dec. 22, 1994) and is expressly incorporated by reference herein. The application discloses an array consisting of four pairs of comb-shaped interdigitated anodes and cathodes serially arranged on a planar silicon chip. Particular circumstances may, of course, require that more or fewer electrodes are mounted in an array. For instance, planar counter and reference electrodes of the type commonly used in electrochemical cells may be arranged besides the interdigitated electrodes. Conductors connecting the electrodes to electrical contact surfaces are covered by an insulating layer.

Referring now to FIG. 1, a schematic presentation describing a pair of enzyme-linked immunoassays which exemplify and compare the use of optical and electrochemical reporter systems is shown.

As shown in FIG. 1, each member of the paired immunoassays is first coated with HIV p24 as an antigenic substrate. Each of the immunoassay pairs is then incubated with serum from HIV positive volunteers which contain antibodies to p24, thereby affording complexation of anti p24 antibodies with a target antigen substrate. Each member of the paired immunoassays is then incubated with goat anti-human immunoglobulin conjugated to biotin. At this point, one of the paired immunoassays is treated with 1) avidin/horseradish peroxidase conjugate and the other paired immunoassays is treated with beta galactosidase/ avidin conjugate producing matched immunoassays with optical and electrochemical reporters respectively.

Figure 3:
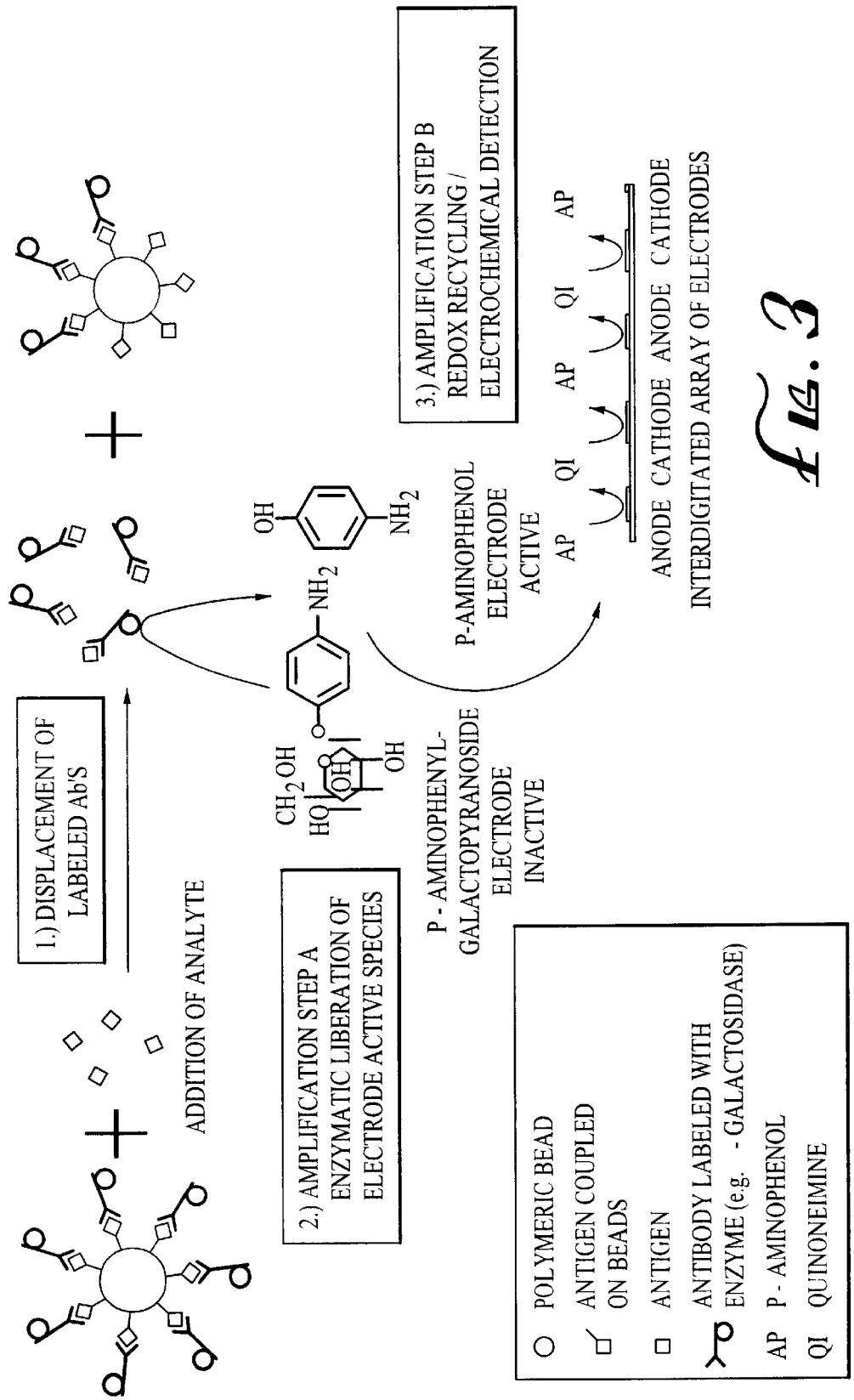

Referring now to FIG. 3, an enzyme-linked immunoassay and electrochemical detection in accordance with the invention is shown. In the first step, unlabeled antigen is bound to a solid phase matrix in a well-known manner. The solid phase matrix may be glassy or polymeric beads, micro titer plates, porous or impervious or even fibrous matrices or membranes or the like, as is well-known in the art. Binding of the antigen or protein to the matrix may be accomplished non-specifically by absorption or covalently by any of the well-known chemical coupling methods. The antigen may be a specific composition of any of the HIV proteins, either recombinant or isolated, or a viral lysate or peptide, or a specific composition of HIV peptides and proteins.

The second step involves attaching antibody having one or more enzyme labels, such as $\beta$-galactosidase or alkaline phosphatase either covalently or by an affinity bond (ionic, hydrogen or hydrophobic, as the case may be) until maximum saturation of the binding site has been reached. The antibodies may be HIV-antibodies, either whole and/or different fragments thereof, with or without hybrid epitope recognition sites, recombinantly expressed, or viral libraries or from immunized animals. They may be of a single class of antibody or a defined mixture of antibodies of different classes with comparable or specific antigen affinities.

The third step requires a sample of body fluid containing the analyte such as HIV antibodies of the kind referred to above to be added. Following an appropriate incubation period and washing steps, a substrate such as p-aminophenyl-g-galactopyranoside is added. Where $\beta$-galactosidase is used as the enzyme label of the antibody, the resulting product is p-aminophenol.

The quantity of p-aminophenol produced is indicative of the concentration of antibody in the specimen and can be measured using an array of interdigitated micro electrodes when the p-aminophenol reacts at the interdigitated anodes and cathodes thereof in a redox process repeatedly alternating between the p-aminophenol and quinoneimine.

Preferably, when the p-aminophenol reacts at the interdigitated anode and cathode of the microelectrode, a redox reaction repeatedly generated between p-aminophenol and the corresponding quinone. Detection or measurement of current may then be accomplished by following an endpoint or kinetic amperiometry. In other words, the current generated by the redox reaction may be measured after a certain time following commencement of the redox operation, or it may be performed dynamically by measuring the rise in current.

Referring now to FIG. 2, a capture immunoassay including the application of multiple bonded enzymes of biotin-avidin conjugates as a method of further signal amplification in accordance with the invention is shown. Initially, antigen, purified HIV p24, is bound to a solid phase carrier matrix Immulon II 96-well Microtiter plates (Dynal Corporation). Subsequently, plasma from uninfected volunteers or HIV seropositive patients containing α-p24 antibodies, are added to complex with the p24 antigens bound to the solid matrix. In the next step, an affinity ligand conjugate is added and allowed to bind before a polyvalent affinity receptor labeling conjugate is introduced. Finally, an enzyme substrate, for example, p-aminophenol-β-galactopyranoside is allowed to react with the labeling enzymes to produce a large quantity of p-aminophenol which when subjected to redox recycling on the interdigitated array of anodes and cathodes of a microelectronic sensor will recycle between p-aminophenol and quinoneimine, thus delivering a strong electrical signal indicative of the concentration of antibody present in the specimen.

It will be appreciated by those skilled in the art that the immunochemical aspects of the above embodiments require certain preparatory steps which included, at least, the following:

The antigen was bound to the solid phase matrix in a glycine buffer coating solution prepared by adding reconstituted p24 (Intracel, Inc.) to the-coating buffer solution to a concentration of 5 μg/ml of p24.

Washing buffer solutions were applied consisting of Dulbecco's phosphate buffered saline solution of pH 7.4 (DPBS free of calcium and magnesium) obtained from BioWhittaker and containing 137 mM of sodium chloride, 3 mM of potassium chloride, a mM of sodium hydrogen phosphate and 1.5 mM of potassium dihydrogen phosphate.

Antibody was diluted in a buffer consisting of DPBS with 1% (weight/volume) of bovine serum albumin, heat shock quality (Jackson) and 0.01% (w/v) Tween 20 (10% w/v) (Boehringer).

Blocking buffer and solution was prepared from DPBS with 5% (w/v) of bovine serum albumin as above and 0.01% (w/v of Tween 20 (10% w/v) (Boehringer).

The enzyme substrate buffer was prepared from 100 mM of sodium chloride in 100 n mM of sodium phosphate buffer at pH 7.25. The enzyme substrate solution was made by dissolving p-aminophenol-β-D-galactopyranoside (Sigma) at a molarity of 1.5 mM in the enzyme substrate buffer.

Figure 4:
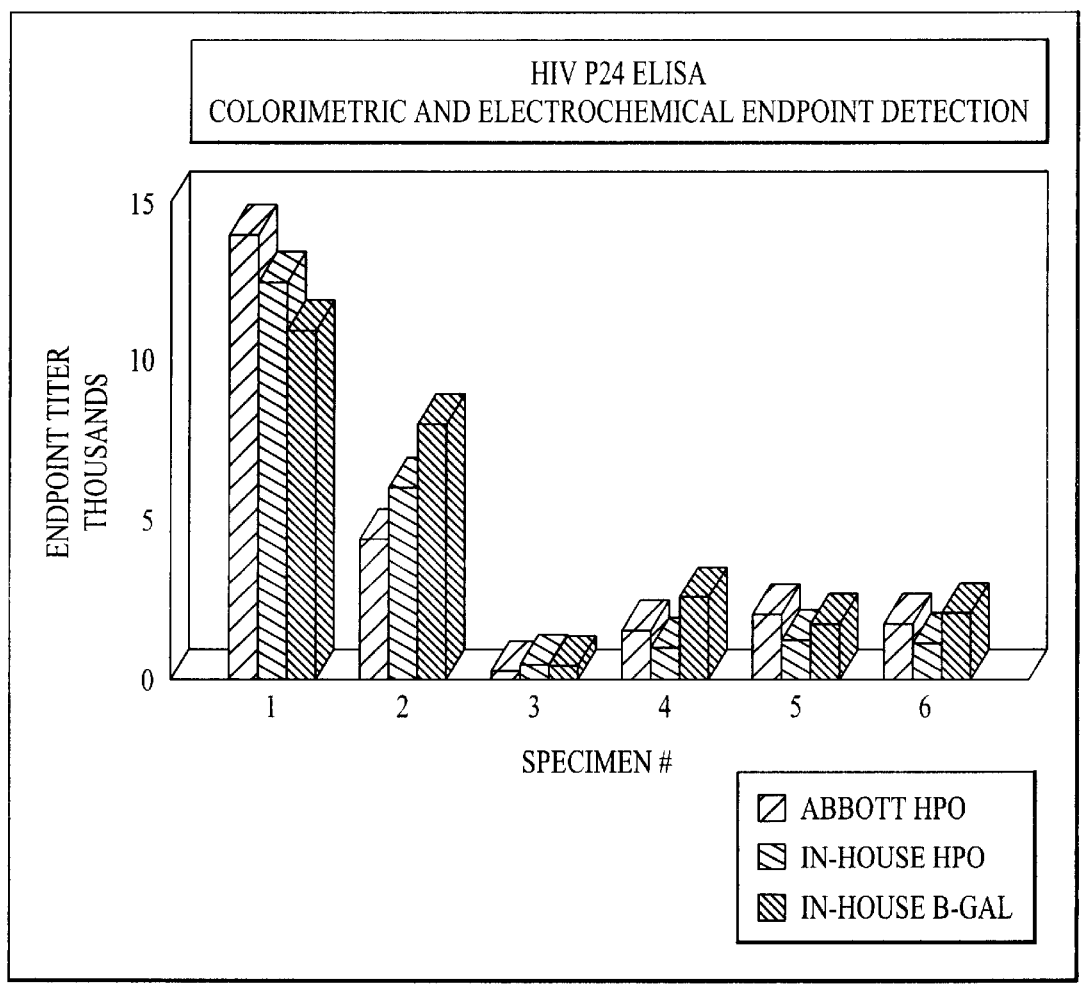
FIG. 4 is a chart comparing results from six different patients as measured (from left to right in each column) with an indigenous optical system, the electrochemical system in accordance with the invention, and a commercially available assay.

Referring now to FIG. 4, a schematic presentation of the invention as applied to the detection of p24 antibody in serum is shown. Preferably, recombinant p24 was non-unspecifically bound by absorption to wells of highly adsorptive micro titer plates by incubating 50 μl of the above coating solution for 2 hours at 37° Celsius. Alternately, microtiter plate coating could be accomplished by overnight incubation at 4° Celsius. The wells were then washed twice with 150 μl of the above washing buffer at room temperature and thereafter blocked with 100 μl blocking solution for 2 hours at room temperature. During this time the samples were repeatedly shaken.

Thereafter, the wells were again washed three times at room temperature, with 150 μl of the patients' serum diluted with dilution buffer at factors ranging between 1:30 and 1:30,000 added and incubated at 37° Celsius for 1 hour. The wells were then washed three times with 150 μl washing buffer at room temperature. 50 μl of a solution containing biotinylated Fc-Fab$_2$ antibody fragments (Jackson) diluted 1:10,000 in dilution buffer were added to each well to detect specifically bound p24 antibody and incubated at 37° Celsius for 1 hour. The wells were then again washed three times with 200 μl of washing buffer at room temperature. 50 μl of avidinD-β-galactosidase conjugate (Vector). C-10 μg/ml diluted in dilution buffer was added and incubated for 0.5 hour at room temperature to detect specifically bound biotinylated Fc-Fab$_2$1 antibody fragments. After washing the wells three times with 150 μl of washing buffer at room temperature, 170 μl of the enzyme substrate solution was added to the wells.

After incubation for about 30 minutes to free the electrochemically redox active p-aminophenol from the p-aminophenol-β-D-galactosidase, the respective supernatants were individually aspirated and transferred to 1 ml sealable plastic vials. To neutralize any remaining residual enzyme activity the vials were incubated at 80° Celsius in a water bath for 10 minutes and were cooled in ice water to room temperature. For a maximum neutralization or inactivation of the activity of the avidin D-β-galactosidase, the inactivation temperature was determined for the bound avidin D-β-galactopyranoside.

The inactive or neutralized supernatant was then transferred to a flow chamber at the bottom of which the microsensor was positioned so as to determine any redox current resulting from the recycling of the enzymatically freed p-aminophenol. Relative to a silver/silver chloride reference electrode, a potential of +250 mV was applied to the anodes of the interdigitated thin-film metal electrodes and a potential of −50 mV is applied to the cathodes. The measurable anode and cathode currents were found to correspond to the presence and quantity of specifically bound antibody to p24.

The redox current clearly distinguished between positive and negative blood samples, and in the positive blood samples it proportionally reflected differences in concentration of p24 antibodies in the serum specimens. In all instances, the electrochemically measured signals corresponded to results obtained by optical read-outs of the same samples. For control purposes, endpoint titers obtained by optical state of the art enzyme-linked immunosorbent assays as disclosed in Abbot Laboratories' Enzyme Immunoassay for the Detection and Semiquantitation of Antibody to the p24 (core) Protein of the Human Immunodeficiency Virus Type 1 (HIV-1) in Human Serum or Plasma (hereinafter "Abbot Immunoassay," a copy of which is attached as Technical Appendix, the Technical Appendix being incorporated herein by reference in its entirety) and by the method in accordance with the invention were compared with each other and were found to differ insignificantly.

Figure 5:
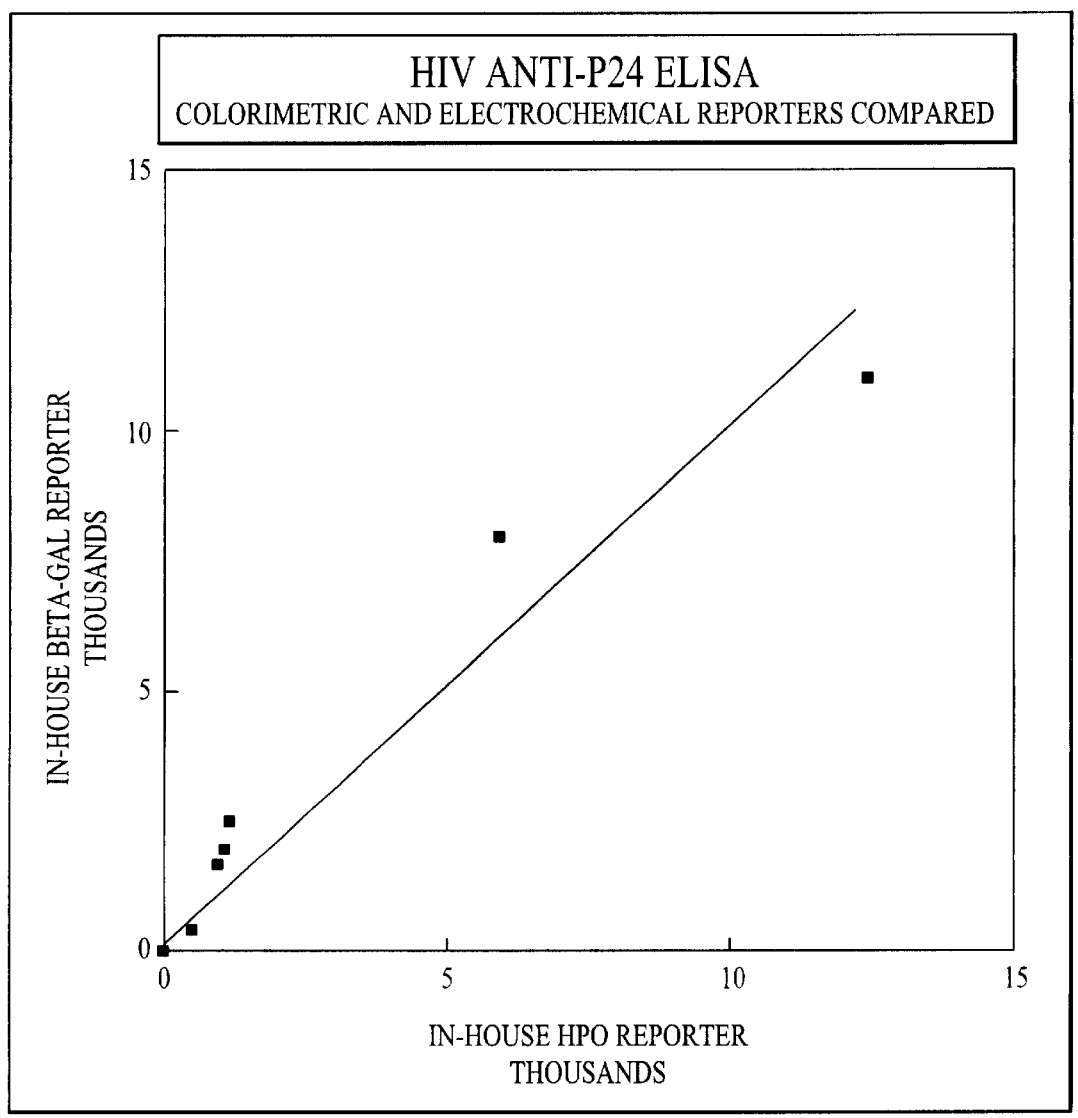
FIG. 5 is a chart which graphically and statistically compares results derived using paired immunoassays which differ in the reporter conjugate employed. An electrochemical reporter in accordance with the invention is used in one immunoassay, and an optical reporter is used in the comparative immunoassay.

Referring now to FIG. 4, a chart comparing the results of measuring endpoint titers performed on samples obtained from six different HIV seropositive patients as measured (from left to right in each column) with an indigenous optical system, the electrochemical system in accordance with the invention, and a commercially available assay, is shown. One measurement (the left column in the figure) was performed with optical read-out by an indigenously developed reference or comparative p24 immunoassay. Another measurement (the right column in the figure) was performed with a commercial Abbott immunoassay, and one measurement (the middle column in the figure) was taken electrochemically by the method in accordance with the invention. The results of the three measurements will be seen to be substantially identical for each patient. The endpoint titer reflects the dilution factor of the serum where the detectable signal obtained with the HIV positive serum is equal to the mean plus or minus two times the standard deviation relative to signals generated when multiple HIV negative serum samples are similarly analyzed. Paired results and regression analyses are presented in FIG. 5. Both correlation coefficient (R squared) and the slop of the least squares best fit line approach 1.0, attesting the comparability of results derived by the optical and electrochemical reporter methods.

Molecular Biology

The present invention is also capable of endpoint detection or kinetic monitoring molecular biology procedures including analytical and clinical applications. The same interdigitated arrays mentioned above can be used to detect voltammetric signals produced in proportion to the concentration of organic (or inorganic) reporter molecules capable of exhibiting redox recycling at the electrode's surface.

These electrochemical labels may be (1) produced as nucleic acid amplicon conjugates which are generated during the replication of selected templates in conjunction with procedures which are exemplified, but not necessarily limited to, PCR (polymerase chain reaction), LCR (ligase chain reaction), NASBA (nucleic acid sequence based amplification), SDA (strand displacement amplification), TAS (transcription based amplification system), 3SR (self-sustained sequence replication) and Q-beta replicase systems; (2) used as substrate moieties or directly conjugated to the complex multiple termini of poly-branched nucleotide targeting probes utilized in signal amplification methods for the detection of specific nucleotide sequences (e.g.: branched Chain DNA technology); or (3) the electrochemically reactive reporters or associated enzymes labels may be directly conjugated to specified nucleic acid reactants or products.

In a molecular biology embodiment, an enzyme mediated electrochemical reporter system, utilizing the IDA previously described, was applied to an analytical method for the detection and quantitation of nucleic acid fragments. In particular, the example used to illustrate the system's general applicability in this field compared the use of the novel electrochemical reporter system to a commercially available and FDA approved polymerase chain reaction (PCR) methodology for the quantitation of HIV RNA in human plasma.

A pair of HIV Monitor' kits produced by Roche Molecular Systems (Branchberg, N.J.) were each applied per instructions contained in the package insert, (a copy of which is attached hereto as Technical Appendix, the Technical Appendix being incorporated herein by reference in its entirety) to a series of five plasmas from HIV seronegative volunteers and nine plasmas obtained from HIV patients. For one kit, all preparation, amplification and detection systems were processed entirely per the instructions contained in the package insert. Detection of the resulting PCR product, however, was accomplished using an avidinated-beta galactosidase conjugate (10 Mg/ml avidin D-β-galactosidase, Vector Labs, Burlingame, Calif.) dissolved in phosphate buffered saline (pH 7.4) PBS with 1% BSA and 0.01% Tween 20 which bound in solution to the biotinylated amplicons. The labeled nucleic acid-enzyme complexes were then separated from solution by hybridization to capture oligomers anchored to the microtiter plate-wells (RMS monitor™).

Figure 6:
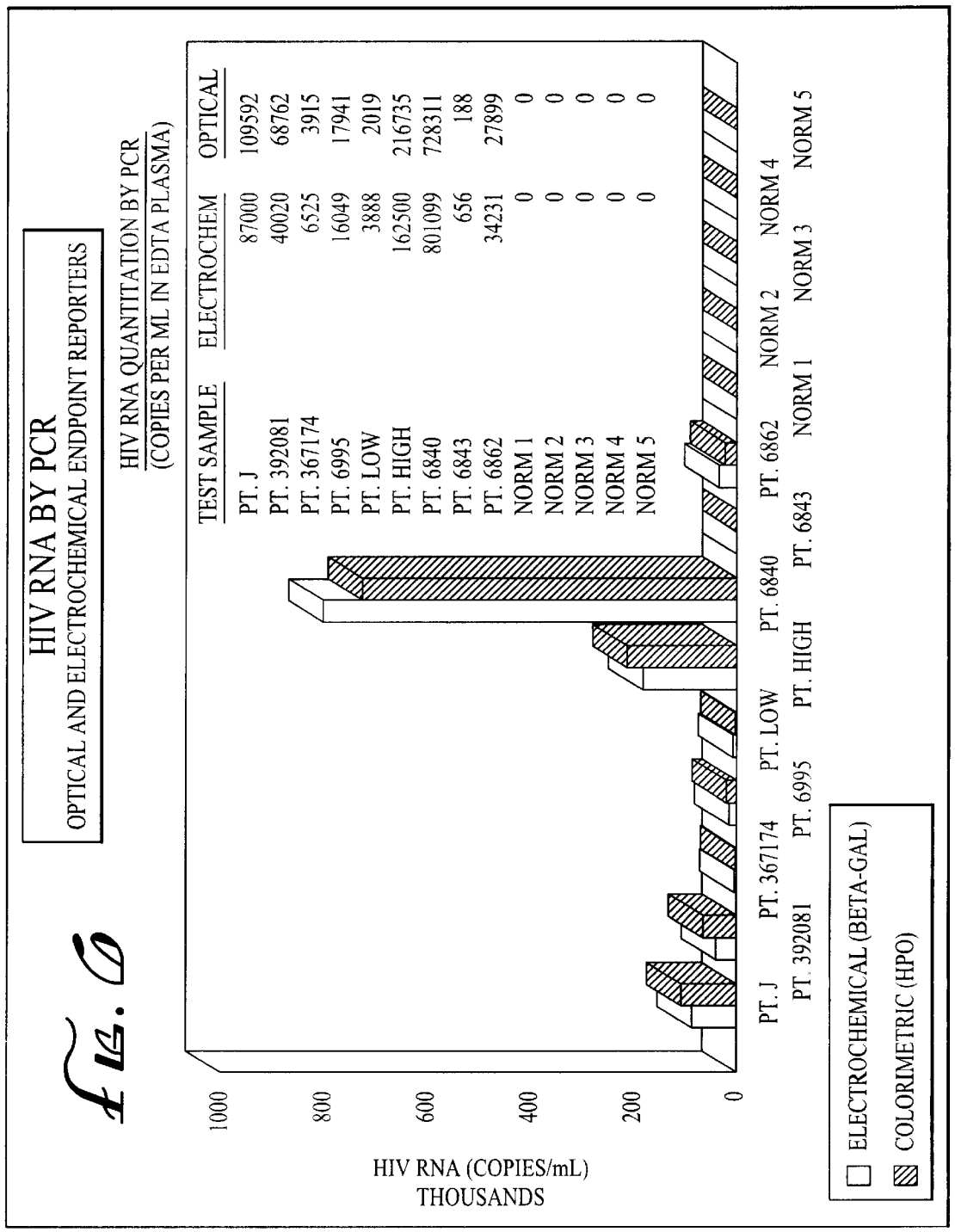
FIG. 6 is a chart presenting quantitative HIV RNA results from fourteen human subject plasmas(from left to right in each column) following (1) RT PCR with amplicons quantitated using an electrochemical system in accordance with the invention, and (2) with amplicons quantitated using an optical reporter system.
Figure 7:
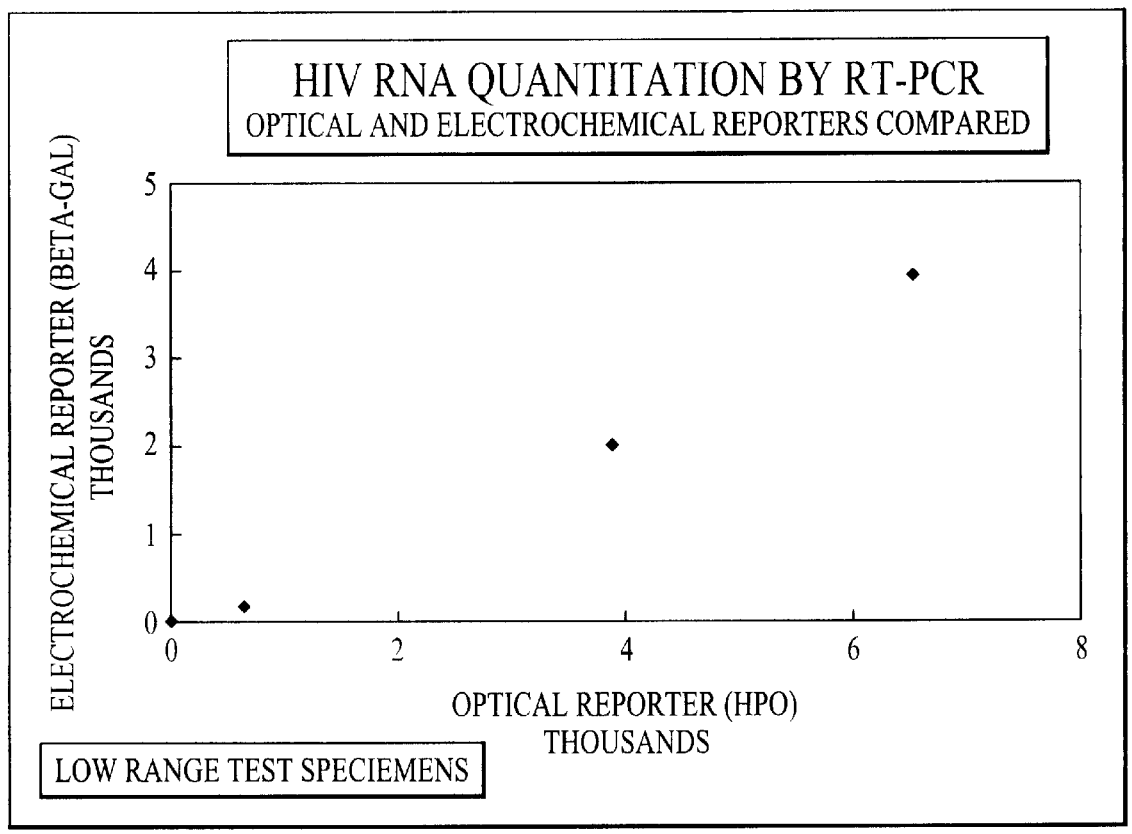
Figure 8:
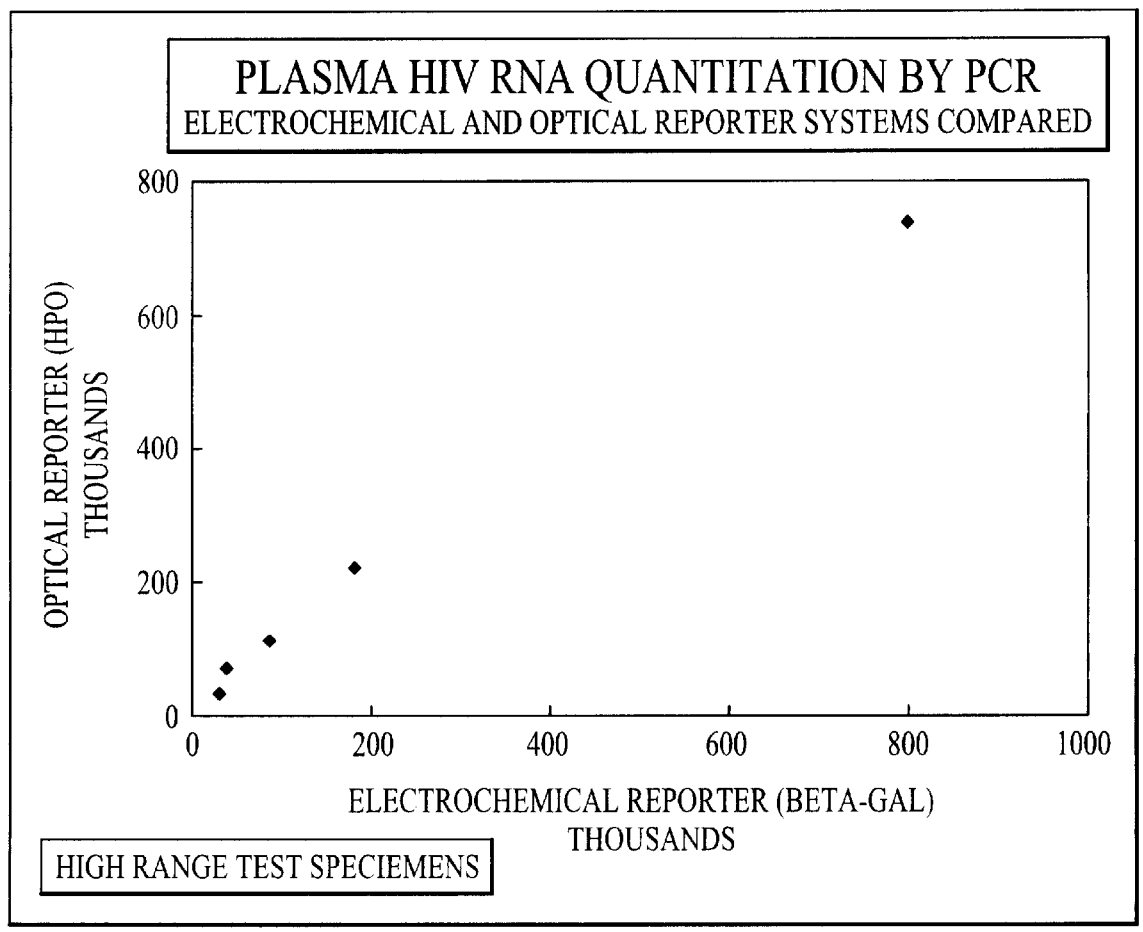

Following incubation with substrate, β-galactopyranoside (60 mM p-aminophenol-β-D-galactopyranoside, Sigma Chemical, St. Louis, Mo.) dissolved in PBS, 7.4), the resulting electrochemically active product (PAP) was measured amperiometrically utilizing the interdigitated micro electrode array. Paired results are presented in FIG. 6 and regression analyses are presented in FIGS. 7–9. Both the correlation coefficient (R squared) and the slope of the least squares best fit line approach 1.0, attesting to the comparability of results derived by the optical and electrochemical reporter methods.

Side by side analyses of HIV-1 negative and HIV-1 positive human plasma samples were carried out using the RMS Monitor procedure per the package insert as well as utilizing the electrochemical reporter modification. Comparison of the results demonstrated the analytic comparability of the two methods. The electromechanical method, is equally applicable as a simple modification to all currently available enzymatically mediated or direct optical reporter methods, and in a manner similar to aforementioned immunoassay applications, substantially simplifies the detector requirements attending conventional calorimetric or chemiluminscent conjugates.

Such methods are currently used commercially for assaying a wide range of specific microbe/virologic and genetic RNA and DNA sequences. In each case, these methods are readily amenable to the minor chemical modification necessary to afford general substitution by electrochemical reporter detection and quantitation using the interdigitated micro electrode array as previously described.

It will be appreciated by those skilled in the art that, the present invention which utilizes thin-film microelectrode arrays and redox recyclable reporter molecules is also applicable, in general, to the examination of tissue, blood or other body fluids for the presence of nucleic acids associated with: 1) infectious diseases; 2) autoimmune diseases; 3) malignancy; 4) inherited diseases; 5) maternity/paternity identification. It will be equally well appreciated by those skilled in the art that the present invention can also be used in both basic research and applied science procedures conducted outside the clinical setting in a broad range of disciplines exemplified, but not limited to: 1) forensic science; 2) basic cellular and developmental biology; 3) archeology and paleontology; and 4) the wide range of animal and plant biotechnologies employing recombinant DNA procedures.

It will be appreciated by those skilled in the art that, the present invention which utilizes thin-film microelectrode arrays and redox recyclable reporter molecules is also applicable to the examination of blood, body fluids, or tissues for the purpose of detecting and measuring the following: 1) free or complex immunoglobulins associated with health or disease (infection or autoimmunity); 2) the presence of antigens related to normal and abnormal developmental processes, (infectious or autoimmunity); 3) presence or absence of specific nucleotide sequences associated with normal or abnormal genetic development, malignancy, or infectious disease.

Having described and illustrated the principles of our invention with reference to a preferred embodiment, it will be apparent that the invention can be modified in arrangement and detail without departing from such principles. As such, it should be recognized that the detailed embodiment is illustrative only and should not be taken as limiting the scope of our invention. Rather, we claim as our invention all such embodiments as may fall within the scope and spirit of the following claims and equivalents thereto.

We claim:

1. An electrochemical reporter system comprising:
  (a) a recognition molecule capable of specifically binding an analyte in a structure restricted manner;
  (b) an enzyme;
  (c) a coupling element, for coupling with specificity the enzyme to the recognition molecule or the analyte;
  (d) a substrate which in the presence of the enzyme is cleavable into a reporter molecule capable of exhibiting redox recycling; and (e) a sensor for detecting the electrochemical reporter molecule, said sensor having a configuration such that the reporter molecule will exhibit redox recycling.

2. The electrochemical reporter system of claim 1, the sensor being a microelectronic interdigitated array of electrodes with a distance between the electrodes of about 100 to about 800 nanometers.

3. The electrochemical reporter system of claim 2, the sensor being a microelectronic interdigitated array of electrodes having a distance between the electrodes of about 300 nanometers.

4. The electrochemical reporter system of claim 1, the recognition molecule being selected from the group consisting of immunoglobulin, fragments of immunoglobulin, non-immunoglobulin binding proteins, and non-biologic binding molecules.

5. The electrochemical reporter system of claim 1, the enzyme being capable of effecting the cleavage of a covalent bond of the substrate.

6. The electrochemical reporter system of claim 5, the enzyme being selected from the group consisting of α-galactosidase, β-galactosidase, α-glucosidase, β-glucosidase, α-mannosidase, β-mannosidase, acid phosphatase, alkaline phosphatase and phosphodiesterase II.

7. The electrochemical reporter system of claim 1, the substrate being selected from the group consisting of p-aminophenyl-β-D-galactopyranoside, p-aminophenyl-α-D-galactopyranoside, p-aminophenyl-α-D-glucopyranoside, p-aminophenyl-β-D-glucopyranoside, p-aminophenyl-α-D-mannopyranoside, p-aminophenyl-β-D-mannopyranoside, p-aminophenylphosphate, and p-aminophenylphosphorylcholine.

8. The electrochemical reporter system of claim 1 wherein the coupling element is selected from the group consisting of:
(a) biotin conjugated to an antibody specific for the recognition molecule or the analyte and avidin conjugated to the enzyme;
(b) biotin conjugated to an antibody specific for the recognition molecule or the analyte and streptavidin conjugated to the enzyme;
(c) digoxigenin conjugated to an antibody specific for the recognition molecule or the analyte and digoxigenin-specific antibody conjugated enzyme
(d) by cross-linking the enzyme to the recognition molecule; and
(e) by cross-linking the enzyme to an antibody specific for the recognition molecule.

9. The electrochemical reporter system of claim 1 wherein the substrate is cleaved into at least one component comprising para-aminophenol.

10. The electrochemical reporter system of claim 1 wherein the sensor is a microelectronic interdigitated array of electrodes having width between about 100 and about 800 nanometers and spaced between about 100 and about 800 nanometers from each other.

11. An electrochemical immunoassay for detecting an analyte in a sample comprising the steps of:
(a) having linked to a surface an antigen with an antibody specific for an analyte bound to the antigen, the antibody being coupled to an enzyme or having a coupling element for being specifically coupled to an enzyme;
(b) contacting the surface with a sample to be analyzed;
(c) collecting the antibodies displaced from the antigen by the analyte in the sample;
(d) adding a substrate to the collected antibodies, said substrate being cleavable by the enzyme into an electrochemical compound; and
(e) measuring the presence or amount of the electrochemical compound with an interdigitated array of electrodes capable of producing redox recycling of the electrochemical compound.

12. An electrochemical immunoassay for detecting an analyte in a sample comprising the steps of:
(a) having linked to a surface an antibody specific for an analyte and an antigen bound to the antibody, the antigen being coupled to an enzyme or having a coupling element for being specifically coupled to an enzyme;
(b) contacting the surface with a sample to be analyzed;
(c) collecting the antigen displaced from the antibody by the analyte in the sample;
(d) adding a substrate to the collected antigen, said substrate being cleavable by the enzyme into an electrochemical compound; and
(e) measuring the presence or amount of the electrochemical compound with an interdigitated array of electrodes capable of producing redox recycling of the electrochemical compound.

13. An electrochemical immunoassay for detecting a specific analyte in a sample comprising the steps of:
(a) having a recognition molecule linked to a non-magnetic surface, said recognition molecule capable of specifically binding the analyte in a structure restricted manner;
(b) contacting the non-magnetic surface with a sample to be analyzed;
(c) coupling with specificity an enzyme to the recognition molecule or the analyte;
(d) adding a substrate, which in the presence of the enzyme is cleaved into a reporter molecule capable of exhibiting redox recycling; and
(e) measuring the presence or amount of the reporter molecule with an interdigitated array of electrodes capable of producing redox recycling of the reporter molecule.

14. The electrochemical immunoassay of claim 13 wherein the enzyme is coupled with specificity to the recognition molecule or the analyte by having the enzyme be avidin- or streptavidin-conjugated and a biotin labeled antibody specific to the recognition molecule or analyte.

15. An electrochemical reporter system comprising:
a) an enzyme;
b) a coupling element, for coupling the enzyme to a nucleotide, oligonucleotide, branched oligonucleotide, nucleic acid, or analogs thereof;
c) a substrate, which in the presence of the enzyme is cleavable into a reporter molecule capable of exhibiting redox recycling; and
d) a sensor for detecting the reporter molecule, the sensor having a configuration such that the reporter molecule exhibits redox recycling.

16. The electrochemical reporter system of claim 15, the sensor being a microelectronic interdigitated array of electrodes with a distance between the electrodes of between about 100 to about 800 nanometers.

17. The electrochemical reporter system of claim 16, the distance between the electrodes being about 300 nanometers.

18. The electrochemical reporter system of claim 15, the enzyme being capable of effecting the cleavage of a covalent bond of tie substrate.

19. The electrochemical reporter system of claim 18, the enzyme being selected from the group consisting of α-galactosidase, β-galactosidase, α-glucosidase, β-glucosidase, α-mannosidase, β-mannosidase, acid phosphatase, alkaline phosphatase and phosphodiesterase II.

20. The electrochemical reporter system of claim 15, the substrate being selected from the group consisting of p-aminophenyl-β-D-galactopyranoside, p-aminophenyl-α-D-galactopyranoside, p-aminophenyl-α-D-glucopyranoside, p-aminophenyl-β-D-glucopyranoside, p-aminophenyl-α-D-mannopyranoside, p-aminophenyl-β-D-mannopyranoside, p-aminophenylphosphate, and p-aminophenylphosphorylcholine.

21. The electrochemical reporter system of claim 15, the coupling element being selected from the group consisting of
   a) a covalent bond;
   b) biotinilated nucleotide, oligonucleotide, branched oligonucleotide, nucleic acid, or analogs thereof and avidin or streptavidin conjugated enzyme; and
   c) digoxigenin labeled nucleotide, oligonucleotide, branched oligonucleotide, nucleic acid, or analogs thereof and digoxigenin-specific antibody conjugated enzyme.

22. The electrochemical reporter system of claim 15, the substrate being cleaved into at least one component comprising pari-aminophenol.

23. The electrochemical reporter system of claim 15, the sensor being a microelectronic interdigitated array of electrodes, wherein the electrodes have a width between about 100 and about 800 nanometers and wherein the electrodes are spaced between about 100 and about 800 nanometers from each other.

24. An assay for detecting or quantitating a specific nucleic acid sequence in a sample comprising the steps of:
   a) having a first single stranded nucleic acid having a sequence complementary to a first segment of the specific nucleic acid sequence to be detected or quantified, the first single stranded nucleic acid being in a solution and bound to a surface;
   b) contacting the first single stranded nucleic acid with a sample to be analyzed;
   c) adding a labeled second single stranded nucleic acid to the sample to be analyzed, said second nucleic acid having a sequence complementary to a second segment of the nucleic acid sequence to be detected or quantified;
   d) adding a substrate, said substrate in the presence of the second single stranded nucleic acid being cleaved into an electrochemical compound; and
   e) detecting the presence or measuring the amount of electrochemical compound present in the solution with an interdigitated array of electrodes capable of producing redox recycling of the electrochemical compound.

25. An electrochemical assay for detecting or quantitating a specific nucleic acid sequence in a sample comprising the steps of:
   a) amplifying the specific nucleic acid sequence in the presence of labeled nucleotides or labeled primer oligonucleotides such that the labeled nucleotides or the labeled primer oligonucleotides are incorporated in labeled newly synthesized nucleic acid;
   b) adding a substrate, said substrate in the presence of the labeled newly synthesized nucleic acid being cleaved into an electrochemical compound; and
   c) measuring the presence or amount of the electrochemical compound present with an interdigitated array of electrodes capable of producing redox recycling of the electrochemical compound.

* * * * *